United States Patent
Fankhauser et al.

(10) Patent No.: US 7,071,366 B2
(45) Date of Patent: Jul. 4, 2006

(54) PROCESSES FOR OBTAINING (-)-GUAIOL AND THE USE THEREOF

(75) Inventors: Peter Fankhauser, Ettingen (CH); Gerd Heinemann, Schliengen (DE); Victor Paul Eliu, Lörrach (DE); William Robert McGilvray, Coraki (AU)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/061,897

(22) Filed: Feb. 18, 2005

(65) Prior Publication Data

US 2005/0143474 A1    Jun. 30, 2005

Related U.S. Application Data

(63) Continuation of application No. 10/181,334, filed as application No. PCT/EP01/00414 on Jan. 16, 2001, now abandoned.

(30) Foreign Application Priority Data

Jan. 20, 2000  (EP) ................... 00810046
Sep. 29, 2000  (CH) ................... 1909/00

(51) Int. Cl.
  *C07C 35/22*  (2006.01)
  *C07C 35/28*  (2006.01)
(52) U.S. Cl. ................. 568/819; 424/725; 424/769; 424/775
(58) Field of Classification Search ........... 424/725, 424/769, 775; 568/819
See application file for complete search history.

(56) References Cited

FOREIGN PATENT DOCUMENTS

AU   75075/98   1/1999
WO   00/04871   2/2000

OTHER PUBLICATIONS

Torul et al "Terpene hydrocarbons of soxhlet and supercritical-gas extracts of oriental spruce and oriental beech" Holzforschung (1984) vol. 38 iss,No. 4, pp. 221-224.*
Thompson and Johnson: "Traditional Bush Medicine, An aboriginal Pharmacopoeia", Greenhouse Publications, Victoria, Australia XP002141573 1988.
Chemical Abstr. 45:12198 for Harris et al., Museum Tech. & Appl. Sci. (1950), 2, 15.

* cited by examiner

*Primary Examiner*—Herbert J. Lilling
(74) *Attorney, Agent, or Firm*—Kevin T. Mansfield

(57) ABSTRACT

A process for obtaining oils of sesquiterpenes and sesquilactones and (–)-guaiol from the oil of *Callitris intratropica*, processes for encapsulation of the oil from *Callitris intratropica*, and the various uses of the oil and the encapsulated oil are described.

The oils are suitable for various purposes in the personal care field, e.g. for the antimicrobial treatment of skin, mucosa and hair and of textile fiber materials, as an antimycotic against skin fungi and moulds, as an anti-inflammatory, as an acaricide against house dust mites and ticks, and for preserving cosmetic products.

6 Claims, No Drawings

PROCESSES FOR OBTAINING (−)-GUAIOL AND THE USE THEREOF

This application is a continuation of application Ser. No. 10/181,334, filed Jul. 17, 2002, now abandoned, which is the National Stage of International Application PCT/EP 01/00414, filed Jan. 16, 2001.

The present invention relates to a process for obtaining (−)-guaiol from the oil of *Callitris intratropica*, to processes for encapsulation of the oil from *Callitris intratropica*, and to various uses of the oil or the encapsulated oil.

Recently there has been a noticeable trend towards the increasing use of active substances of natural origin in the field of cosmetics. For example, essential oils, e.g. tea tree oil, are being used in aromatherapy or in the manufacture of products in the personal care field.

From the wood and/or bark of *Callitris intratropica* (Australian Blue Cypress), a species native to relatively warm climatic zones, e.g. Northern Australia, which is mainly cultivated in plantations, it is possible to obtain an oil consisting of several fractions, which is called "blue oil" because of its intrinsic colour. The blue colour of the oil from *Callitris intratropica*, as is also the case with other oils (e.g.: camomile oil, patchouli oil), is caused by (s)-guaiazulene (1,4-dimethyl-7-isopropylazulene).

An essential fraction of this oil is (−)-guaiol, a sesquiterpene alcohol, which corresponds to the formula

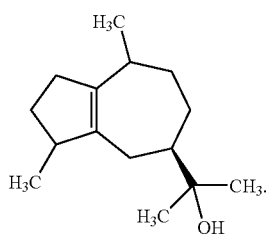

(1)

Guaiol has optical isomers; the compound of formula (1) corresponds to the (−) form.

The present invention accordingly relates to a process for obtaining (−)-guaiol corresponding to formula (1) from the oil of *Callitris intratropica*, in which process the oil is held at about from 4 to −18° C. and the (−)-guaiol which then separates out in the form of fine needles is isolated from the rest of the oil by filtration and then washed with cold, nonpolar solvent.

$C_5$–$C_{10}$Alkanes, and especially n-hexane or iso-octane, are preferably used as the cold, nonpolar solvent.

Solvent mixtures may preferably also be used, especially mixtures of n-hexane/petroleum ether, ethanol/water, dimethylformamide/water, methanol/water, ethylene glycol/water, ethylene glycol methyl and ethyl ester/water, dimethyl sulfoxide/water, tetrahydrofuran/water and dioxane/water.

In an especially preferred embodiment, the (−)-guaiol is isolated from the rest of the oil by filtering under suction.

For further purification, the crude (−)-guaiol obtained may be recrystallised from a solvent mixture selected from n-hexane/petroleum ether, ethanol/water, dimethylformamide/water, methanol/water, ethylene glycol/water, ethylene glycol methyl and ethyl ester/water, dimethyl sulfoxide/water, tetrahydrofuran/water and dioxane/water.

n-Hexane/petroleum ether or a mixture of ethanol/water is preferably used for further purification.

In a further process variant, the crude (−)-guaiol is, after filtration, subjected to vacuum distillation for purification.

In another process variant for obtaining (−)-guaiol, the crude material of *Callitris intratropica*, which is contaminated with other ingredients, is subjected to steam distillation and, for further purification, is recrystallised from a solvent mixture selected from n-hexane/petroleum ether, ethanol/water, dimethylformamide/water, methanol/water, ethylene glycol/water, ethylene glycol methyl and ethyl ester/water, dimethyl sulfoxide/water, tetrahydrofuran/water and dioxane/water.

n-Hexane/petroleum ether or a mixture of ethanol/water is preferably used for further purification.

The oil which has been depleted of (−)-guaiol after filtration can be used for various purposes.

Oils of sesquiterpenes and sesquilactones can also be obtained using supercritical solvents. In that process, pieces of wood with or without bark and/or pieces of bark of *Callitris intratropica*, *glaucophylla* or *columellaris* are extracted with a supercritical solvent.

Suitable supercritical solvents are supercritical media known from the prior art, which are also used for plant extraction, for example supercritical ethylene, propane, butane, pentane, $N_2O$ or $CO_2$, which basically may be used in an identical manner in the context of the present invention.

In a preferred embodiment, the extraction is carried out in mixtures of $CO_2$ and cyclic $C_1$–$C_{10}$hydrocarbons or $C_1$–$C_{10}$-n-alkanes, especially propane, butane and pentane.

Preference is also, however, given to lipophilic extraction with supercritical $CO_2$ and modifiers, such as short-chain aliphatic alcohols, for example ethanol or methanol.

The supercritical solvents are very inert and, because of their high vapour pressure and their volatility, can be completely removed, even at low temperatures, without loss of the more volatile constituents of the extract.

Extraction processes using supercritical media are generally known and commercially available.

Preference is given to the use of bark chips for extraction.

Wood chips and bark chips of *Callitris intratropica*, *glaucophylla* or *columellaris* are extracted at a pressure of from 20 to 2000 bar and at temperatures of from 30 to 80° C. with a supercritical medium, preferably supercritical $CO_2$, propane or butane, and optionally with added amounts of from 0% to 15% of a short-chain aliphatic alcohol, for example methanol or ethanol, over a period of from 30 minutes to 5 hours.

After releasing the pressure, the oil is present in pure form in a yield of from 1 to 10%, based on the weight of wood used.

Compared to steam distillation, the yield of oil is distinctly higher and the oil has a completely different composition of individual components.

It is also possible to obtain (−)-guaiol from the oil obtained by that process, by allowing the (−)-guaiol to crystallise out at room temperature or by freezing it out.

For that purpose, the oil is held at about from 25 to −18° C. A portion of the (−)-guaiol is separated out in the form of fine needles. After filtration, the (−)-guaiol-depleted oil can be used further. The purity of the (−)-guaiol is increased to >98% by recrystallising from aliphatic (including cyclic) hydrocarbons or an ethanol/water mixture.

Solutions of from 30 to 2000 mg/liter in ethanol are prepared from the untreated oil from *Callitris intratropica* and from the (−)-guaiol-depleted oil.

The colourless to slightly yellow oil so obtained exhibits a distinctly greater antimicrobial action than the oil obtained by steam distillation.

The oil obtained from *Callitris intratropica* by the processes according to the invention may advantageously be encapsulated. Suitable encapsulation materials are especially α-, β- and γ-cyclodextrins, liposomes, bacteria, fungi, organic and inorganic porous supports, the latter being selected from bentonites, modified bentonites and hectorites. The invention also relates to the process for encapsulation of the oil from *Callitris intratropica*, in which process equimolar amounts of the oil from *Callitris intratropica* and one of the previously mentioned encapsulation materials are suspended in water and stirred for from 1 to 4 hours until a complex of encapsulation material and oil forms.

If a fungus is used as encapsulation material, typical examples are yeasts, for example *Saccharomyces cerevisiae* (brewer's yeast and baker's yeast), *Kluyveromyces fragilis* (dairy yeast) and *Candida utilis*, and also filamentous fungi, for example *Aspergillus niger*.

The encapsulation material preferably has a cell diameter of, for example, about 5 μm. Bacteria can have a smaller cell size of about from 1 to 2 μm and can be cultured to produce a larger cell diameter.

The oil of *Callitris intratropica* obtained in accordance with the invention exhibits pronounced antimicrobial action, especially against pathogenic gram-positive and gram-negative bacteria and also against bacteria of skin flora, for example *Corynebacterium xerosis* (bacteria that cause body odour), and also as an antimycotic against yeasts and moulds. It is therefore especially suitable in the disinfection, deodorising and general antimicrobial treatment of the skin and mucosa and of integumentary appendages (hair), more especially in the disinfection of the hands and wounds.

It is therefore suitable as an antimicrobial active ingredient in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation containing from 0.01 to 15% by weight, based on the total weight of the composition, of the oil of *Callitris intratropica*, or of the encapsulated oil prepared in accordance with the invention, or of the oil obtained using supercritical solvents or of the (−)-guaiol-depleted oil, and cosmetically tolerable adjuvants.

Depending on the form of the personal care preparation, it comprises—besides the oil of *Callitris intratropica* or the encapsulated oil prepared in accordance with the invention—further constituents, e.g. sequestering agents, colorants, perfume oils, thickening or solidifying (consistency-regulating) agents, emollients, UV absorbers, skin protection agents, antioxidants, additives that improve the mechanical properties, for example dicarboxylic acids and/or aluminium, zinc, calcium and magnesium salts of $C_{14}$–$C_{22}$ fatty acids and, optionally, additional preservatives and antimicrobial active ingredients.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

A water-in-oil or oil-in-water emulsion containing the oil of *Callitris intratropica* preferably contains, as cosmetically tolerable adjuvants, from 5 to 50% of an oily phase, from 5 to 20% of an emulsifier and from 30 to 90% water.

The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

The oil used in accordance with the invention may be contained in a variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose and pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:

0.01 to 5% by weight of the compound of the oil from *Callitris intratropica*,
0.3 to 1% by weight titanium dioxide,
1 to 10% by weight stearic acid and
ad 100% soap base, e.g. the sodium salts of tallow fatty acid and coconut fatty acid or glycerol.

A shampoo has, for example, the following composition:
0.01 to 5% by weight of the oil from *Callitris intratropica*,
12.0% by weight sodium laureth-2-sulfate,
4.0% by weight cocamidopropyl betaine,
3.0% by weight NaCl and
water ad 100%.

A deodorant has, for example, the following composition:
0.01 to 5% by weight of the oil from *Callitris intratropica*,
60% by weight ethanol,
0.3% by weight perfume oil and
water ad 100%.

Example of an O/W Emulsion:
0.01–5% by weight of the oil from *Callitris intratropica*,
12% by weight glyceryl stearate,
6% by weight paraffin oil,
6% by weight caprylic/capric triglyceride,
4% by weight glycerol,
0.2% by weight disodium EDTA,
1.0% by weight citric-acid (20%) and
65.8–70.8% by weight water.

Example of an O/W Emulsion:
0.01–5% by weight of the oil from *Callitris intratropica*,
3.5% by weight PEG-30 dipolyhydroxystearate,
10.0% by weight paraffin oil,
4% by weight caprylic/capric triglyceride,
4% by weight dicaprylic ether,
0.2% by weight disodium EDTA,
3.4% by weight glycerol and
69.9–74.9% by weight water.

The oil of *Callitris intratropica*, or the encapsulated oil prepared in accordance with the invention, or the oil obtained in accordance with the invention, or the (−)-guaiol-depleted oil, is, moreover, used as an anti-inflammatory and also as an acaricide against house dust mites and ticks.

The oil of *Callitris intratropica*, or the encapsulated oil prepared in accordance with the invention, or the oil obtained in accordance with the invention, or the (−)-guaiol-depleted oil, is also suitable for the antimicrobial treatment of textile fibre materials, the latter being undyed or dyed or printed fibre materials, for example of silk, wool, polyamide, polyester, polypropylene or polyurethanes, and especially of all kinds of cellulosic fibre materials. Such fibre materials include, for example, natural cellulose fibres, such as cotton, linen, jute and hemp, and also cellulose and regenerated cellulose. Preferred suitable textile fibre materials are of cotton.

The oil of *Callitris intratropica*, or the encapsulated oil prepared in accordance with the invention, or the oil obtained in accordance with the invention, or the (−)-guaiol-depleted oil, is also suitable for preserving cosmetic products, for example shampoos, bath additives, hair-care preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders and household products, e.g. in washing and cleaning formulations, e.g. in liquid and powder washing compositions or fabric softeners.

The following Examples illustrate, but do not limit, the invention.

EXAMPLES

Example 1

Preparation of Oil, Encapsulated with Cyclodextrin, from *Callitris Intratropica* (ABC)

340 g (30 mmol) of cyclodextrin having a molecular mass of 1134 are suspended in 1 liter of water. 66 g of ABC are added to the suspension and the mixture is stirred for from 4 to 8 hours at room temperature.

Filtration is then carried out through a suction filter and the filter cake is washed with ethanol, dioxane or some other water-miscible solvent in which the oil is readily soluble. The washing procedure is not imperative if free non-encapsulated ABC may remain behind on the product.

The wet filter cake is then dried at about 20 mbar and 100° C. in a drying cabinet or using a paddle dryer.

When preparing smaller amounts, freeze-drying is suitable if moisture contents of less than 5% water are to be obtained.

Example 2

Antimicrobial Action Test

In the microbial test, the extract or fractions of the extract from the wood and/or bark of the Australian Blue Cypress (*Callitris intratropica*) exhibits a pronounced inhibitory action on various fungi of the skin, yeasts and, especially, bacteria. The MIC values (minimum inhibitory concentration) are in a range from 125 to 600 ppm with respect to gram-positive bacteria, e.g. *Staphylococcus aureus, Staphylococcus epidermidis* or *Corynebacterium xerosis*; markedly ≦125 ppm in some cases, with respect to moulds, e.g. A. niger, *Pidermophyton floccosum* and *Trichophyton mentagrophytes*; and 2000 ppm with respect to yeasts, e.g. *Candida albicans*.

Examples (Table 1)

(MIC—Minimum Inhibitory Concentration)

TABLE 1

| Test organism | MIC of pure oil | MIC of 10% oil in cyclodextrin | MIC of pure cyclodextrin |
|---|---|---|---|
| *Porphyromonas gingivalis* | 500 ppm | 250 ppm | >10 000 ppm |

TABLE 1-continued

| Test organism | MIC of pure oil | MIC of 10% oil in cyclodextrin | MIC of pure cyclodextrin |
| --- | --- | --- | --- |
| *Selenomonas artemidis* | 750 ppm | 500 ppm | >10 000 ppm |
| *Staphylococcus aureus* | 250 ppm | 10 000 ppm | >10 000 ppm |
| *Staphylococcus mutans* | 125 ppm | 2000 ppm | >10 000 ppm |
| *Staphylococcus sobrinus* | 125 ppm | 2000 ppm | >10 000 ppm |
| *Malassezia furfur* | 10 000 ppm | 2000 ppm | >10 000 ppm |
| *Epidermophyton floccosum* | 125 ppm | 750 ppm | >10 000 ppm |
| *Microsporum canis* | 60 ppm | 500 ppm | >10 000 ppm |
| *Microsporum gypseum* | 60 ppm | 750 ppm | >10 000 ppm |
| *Trichophyton mentagrophytes* | 60 ppm | 750 ppm | >10 000 ppm |
| *Trichophyton rubrum* | 30 ppm | 750 ppm | >10 000 ppm |
| *Trichophyton schoenleinii* | 60 ppm | 500 ppm | >10 000 ppm |

Formulation Examples for Oils from *Callitris Intratropica* (ABC)

Example 3

Clear Aqueous Solution
  Composition:
  0.01 to 1% ABC,
  0.5% benzyl alcohol,
  1.5 to 3.5% polysorbate 20 or some other non-ionic surfactant,
  0.1% of a chelate-former, e.g. sodium EDTA,
  0 to 5.0% butylene glycol, in distilled water.

Example 4

Shampoo
  0.01 to 1% ABC,
  0 to 0.5% benzyl alcohol,
  8 to 12% sodium lauryl ether sulfate,
  0 to 0.1% disodium EDTA,
  2 to 4% of a betaine (e.g. coco betaine),
  3% coconut diethanolamide,
  0 to 0.1% Polyquaternium-10,
  0 to 0.5% sodium chloride, organic acid (e.g. citric acid 10%) for adjustment to a pH of from 6.0 to 7.0.

Example 5

Hair Conditioner
  0.01 to 1% ABC,
  0 to 0.5% benzyl alcohol,
  2.5 to 3.5% stearyl alcohol,
  0.05% PEG-7 glyceryl fatty acid (e.g. Cetiol HE),
  hydrolysed wheat protein (e.g. Hydrotriticum),
  0.1 to 0.2% citric acid (10%),
  0.1% Panthenol and
  1% cetyl trimethyl ammonium chloride (50%) or some other cationic surfactant, made up to 100% with distilled water.

For preparation of further formulations (Examples 6 to 9), an active ingredient concentrate having the following composition is used as starting material:
  1 to 80% ABC, or mixtures of ABC with other active ingredients, e.g. tea tree oil (TTO),
  5 to 80% of a phenyl-substituted alcohol, e.g. benzyl alcohol,
  0 to 80% of a surfactant (anionic, cationic or amphoteric, but preferably non-ionic, for example polyethylene oxide ester or carboxylic acid ester),
  0 to 80% of a dispersion aid.

An active ingredient content of from 5 to 50%, an alcohol content of from 30 to 50%, a surfactant content of from 30 to 50% and a dispersion aid content of from 20 to 50% are ideal.

Example 6

Example of a Typical Cream
  2% ABC,
  2 to 3% glycerol,
  5% groundnut oil,
  10% of a colloidal dispersion of cetyl stearyl alcohol together with non-ionic emulsifiers based on saturated fatty acid polyglycol ethers (e.g. Emulgate 1000 NI), in water.

Example 7

Example of a Typical Lotion
  2% ABC,
  5% glycerol monostearate A–S,
  3% Emulgin B1,
  5% glycerol,
  2% cetyl alcohol, in water.

Example 8

Example of a Typical Gel
  2% ABC,
  5% glycerol,
  3% Sepigel 305, in water.

Example 9

Example of a Typical Conditioner
  2% ABC,
  2% cetyl alcohol,
  3% cetostearyl alcohol,
  3% Vantoc CC (cetyl trimethyl ammonium chloride),
  5% lauryldiimoniumhydroxypropyl hydrolysed collagen and
  0.5% Dipanthenol.

Exemplary Embodiments

Example 10

The trunk of *Callitris intratropica* comminuted into wood chips and bark chips is comminuted using a suitable mill, preferably a hammer mill or an impact bar mill. Material that has already previously undergone steam distillation (SD) may also be used. 2 kg of the material are subjected to extraction with supercritical $CO_2$ at ≦400 bar (preferably 250 bar) and at from 20 to 60° C. (preferably 45° C.). The duration of the extraction is, depending on pressure and temperature, from 1 to 8 hours, ideally 4 hours.

The main components found were (in GC area %):

| Component | pure oil* from SD | pure oil from SE | pure oil from SFE |
|---|---|---|---|
| (−)-guaiol | 12–14% | 14–16% | 12–15% |
| α-, β-, γ-eudesmols | 13–15% | 6–8% | 6–8% |
| bulnesol | 11–13% | 4–6% | 4–6% |
| β-, γ-costol | <1% | 3–5% | 3–5% |
| dihydrocolumellarins | 8–10% | 28–32% | 28–32% |
| callitrisin | 1–2% | 8–10% | 8–10% |
| columellarin | <1% | 7–9% | 7–9% |

Examples (MIC=Minimum Inhibitory Concentration)

| Test organism | MIC pure oil from SD | pure oil from SE | pure oil from SFE |
|---|---|---|---|
| Aspergillus niger | 31 ppm | 60 ppm | 60 ppm |
| Candida albicans | >10 000 ppm | 125 ppm | 125 ppm |
| Candida tropicalis | >10 000 ppm | 125 ppm | 125 ppm |
| Selenomonas artemidis | 750 ppm | 60 ppm | 60 ppm |
| Staphylococcus aureus | 250 ppm | 60 ppm | 60 ppm |
| Staphylococcus mutans | 125 ppm | 60 ppm | 60 ppm |
| Staphylococcus sobrinus | 125 ppm | 30 ppm | 30 ppm |
| Malassezia furfur | 10 000 ppm | 60 ppm | 60 ppm |
| Epidermophyton floccosum | 125 ppm | 60 ppm | 60 ppm |
| Microsporum canis | 60 ppm | 60 ppm | 60 ppm |
| Microsporum gypseum | 60 ppm | 60 ppm | 60 ppm |
| Propionibacterium acnes | 62 ppm | 30 ppm | 30 ppm |
| Trichophyton mentagrophytes | 60 ppm | 60 ppm | 60 ppm |
| Trichophyton rubrum | 30 ppm | 60 ppm | 60 ppm |
| Trichophyton schoenleinii | 60 ppm | 60 ppm | 60 ppm |

*) after isolating the guaiol that has crystallised out
SD = steam distillation;
SE = solvent extraction;
SFE = supercritical fluid extraction

What is claimed is:

1. A process for obtaining (−)-guaiol, wherein pieces of wood with or without bark and/or pieces of bark of *Callitris intratropica, glaucophylla* or *columellaris* are extracted with a supercritical solvent and the (−)-guaiol is crystallised out at room temperature, or frozen out, from the oil thereby obtained.

2. A process according to claim 1, wherein bark chips are used for the extraction.

3. A process according to claim 1, wherein the supercritical solvent is selected from supercritical $CO_2$, ethylene, propane, butane, pentane and $N_2O$.

4. A process according to claim 1, wherein the supercritical solvent is selected from mixtures of $CO_2$ and cyclic $C_1$–$C_{10}$ hydrocarbons or $C_1$–$C_{10}$-n-alkanes.

5. A process according to claim 1, wherein small amounts of modifiers are additionally used.

6. A process according to claim 5, wherein extraction is carried out with a mixture of $CO_2$ and ethanol or methanol.

* * * * *